(12) United States Patent
Shinohara

(10) Patent No.: US 6,608,018 B1
(45) Date of Patent: Aug. 19, 2003

(54) POLYPEPTIDES HAVING BRANCHING ENZYME ACTIVITY AND NUCLEIC ACIDS ENCODING SAME

(75) Inventor: Mari L. Shinohara, Brookline, MA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/537,120

(22) Filed: Mar. 29, 2000

Related U.S. Application Data

(60) Provisional application No. 60/129,608, filed on Apr. 16, 1999.

(30) Foreign Application Priority Data

Mar. 29, 1999 (DK) .................................. 1999 00431

(51) Int. Cl.$^7$ .............................. C12N 9/10; C11D 3/00
(52) U.S. Cl. ...................................... 510/392; 435/193
(58) Field of Search ....................... 435/193; 536/23.2; 510/392

(56) References Cited

U.S. PATENT DOCUMENTS 4,454,161 A    6/1984  Okada et al. .................. 426/48

FOREIGN PATENT DOCUMENTS

| EP | 0 418 945 A1 | 3/1991 |
| EP | 0 690 170 A1 | 1/1996 |
| EP | 0 710 674 A2 | 5/1996 |
| WO | WO 97/29186 | 8/1997 |
| WO | WO 97/41736 | 11/1997 |

OTHER PUBLICATIONS

Van De Loo et al. (1995) Proc Natl Acad Sci USA 92:6743–6747.*
Seffernick et al. (2001) J Bacteriol 183:2405–2410.*
Boyer et al., Biochemistry, vol. 16, pp. 3693–3699 (1977).
Walker et al., Eur. J. Biochem., vol. 20, pp. 14–21 (1971).
Kiel et al., Gene, vol. 89, pp. 77–84 (1990).
Rumbak et al., Journal of Bacteriology, vol. 173, pp. 6732–6741 (1991).
Kiel et al., DNA Sequence—J.DNA Sequencing and Mapping, vol. 3, pp. 221–232 (1992).
L.P.T.M. Zevenhuizen, Biochim. Biophys. Acta, vol. 81, pp. 608–611 (1964).
Abstract of Japanese Patent No. JP 7213287 A (1995).
Abstract of article by Shvedova et al., Pirkl. Biokhim. Mikrobiol, vol. 14, No. 5, pp. 683–689 (1978).
Takata et al., Applied and Environmental Microbiology, vol. 60, pp. 3096–3104 (1994).
Jespersen et al., Journal of Protein Chemistry, vol. 12, pp. 791–805 (1993).
Takata et al., Carbohydrate Research, vol. 295, pp. 91–101 (1996).
Borovsky et al., Eur. J. Biochem., vol. 59, pp. 615–625 (1975).
Takata et al., The Journal of Biological Chemistry, vol. 267, pp. 18447–18452 (1992).
Matsumoto et al., J. Biochem., vol. 107, pp. 123–126 (1990).
Matsumoto et al., J. Biochem., vol. 107, pp. 118–122 (1990).
Kuriki et al., Journal of Protein Chemistry, vol. 15, pp. 305–313 (1996).
Hisamatsu et al., Starch/Stärke, vol. 41, pp. 239–242 (1989).
Cheong et al., Enzymes for Carbohydrate Engineering (1995).
Kuriki et al., The Journal of Biological Chemistry, vol. 271, pp. 17321–17329 (1996).
Birte Svensson, Plant Molecular Biology, vol. 25, pp. 141–157 (1994).
Abstract of article by Mu–Forster et al., Plant Physiol., vol. 116, pp. 1563–1571 (1998).
Abstract of article by Cheong et al., Prog. Biotechnol. (Enzymes for Carbohydrate Engineering, vol. 12, pp. 43–60 (1996).
Abstract of article by Kobayashi et al., Agric. Biol. Chem., vol. 54, pp. 147–156 (1990).
Abstract of article by Amirul et al., Folia Microbiol. (Prague), vol. 41, pp. 165–174 (1996).
Abstract of article by Matsumoto et al., J. Biochem. (Tokyo), vol. 107, pp. 123–126 (1990).
Abstract of article by Abramsky et al., Biochim. Biophys. Acta, vol. 421, pp. 106–114 (1976).
Abstract of article by Kiel et al., DNA Sequence, vol. 4, pp. 1–9 (1993).
Abstract of Japanese Patent Application JP 09191876 (1997).
Abstract of article by G. Stephanopoulos, Curr. Opin. Biotechnol., vol. 5, No. 2, pp. 196–200 (1994).
Abstract of article by Gaouar et al., Industrial Crops and Products, vol. 7, pp. 159–167 (1998).
Abstract of article by Mathupala et al., Biotechnology Letters, vol. 16, No. 12, pp. 1311–1316 (1994).
Abstract of article by Sakano Yoshiyuki, Shoku ni kansuru Josei Kenkyu Chosa Hokokusho, No. 10, pp. 63–68 (1997).
Abstract of article by Parrou et al., Microbiology–UK, vol. 143, pp. 1891–1900 (1997).
Abstract of Japanese Patent JP 06062881 (1994).

(List continued on next page.)

*Primary Examiner*—Rebecca E. Prouty
*Assistant Examiner*—David J Steadman
(74) *Attorney, Agent, or Firm*—Elias Lambiris; Jason Garbell

(57) ABSTRACT

The present invention relates to isolated polypeptides having branching enzyme activity and isolated nucleic acid sequences encoding the polypeptides. The invention also relates to nucleic acid constructs, vectors, and host cells comprising the nucleic acid sequences as well as methods for producing and using the polypeptides.

18 Claims, No Drawings

OTHER PUBLICATIONS

Abstract of article by Heinrich et al., European Journal of Biochemistry, vol. 243, pp. 191–201 (1997).
Abstract of article by Hoq et al., Applied Microbiology and Biotechnology, vol. 43, pp. 604–609 (1995).
Abstract of article by Tosi et al., Canadian Journal of Microbiology, vol. 39, pp. 846–852 (1993).
Abstract of article by Britton et al., European Jouranl of Biochemistry, vol. 229, pp. 688–695 (1995).
Abstract of article by Loiseau et al., Parasitology, vol. 106, pp. 55–61 (1993).
Abstract of article by Kiel et al., Mol. Gen. Genet., vol. 230, pp. 136–144 (1991).
Abstract of article by Kaidalova et al., Mol. Biol. (Moscow), vol. 24, pp. 1381–1392 (1990).
Abstract of article by Heinrich et al., Bull. Math. Biol., vol. 49, pp. 539–596 (1987).
Abstract of article by Frere et al., Biochem. J., vol. 207, pp. 429–436 (1982).
Abstract of article by Kelly et al., Biochem. J., vol. 199, pp. 137–144 (1981).
Abstract of article by Inagaki et al., Biosci. Biotechnol. Biochem., vol. 59, pp. 535–537 (1995).
Abstract of WO/91/088587 (1991).
Abstract of article by Koch et al., Dechema Biotechnol. Conf., vol. 4, Part A, pp. 245–248 (1990).
Abstract of article by Slodki et al., Develop. Pertrol. Sci., vol. 31, pp. 247–255 (1991).
Abstract of article by Hisamatsu et al., J. Ferment. Technol., vol. 67, No. 3, pp. 219–220 (1989).
Abstract of article by Yalpani et al., Prog. Biotechnol., vol. 3, pp. 7–34 (1987).
Abstract of article by G. Antranikian, Fems Microbiol. Rev., vol. 75, pp. 201–218 (1990).
Abstract of article by Park et al., Progress in Biotechnology, vol. 12, p. 215 (1996).
Abstract of EP 0 487 000 A1 (1992).
Abstract of EP 0 486 936 A1 (1992).
Abstract of EP 0 372 184 A (1990).
Abstract of article by Kaidalova N.V. (Reprint), Molecular Biology, vol. 24, No. 5, pp. 1103–1112 (1990).
Abstract of sequence of article by Kiel et al., Mol. Gen. Genet., vol. 230, pp. 136–144 (1991).
Bruton et al., Molecular Microbiology, vol. 18, pp. 89–99 (1995).
Homerova et al., Biochimica et Biophysica Acta 1200, pp. 334–336 (1994).

* cited by examiner

SEQUENCE LISTING

<160> NUMBER OF SEQ ID NOS: 2

<210> SEQ ID NO 1
<211> LENGTH: 1866
<212> TYPE: DNA
<213> ORGANISM: Rhodothermus obamensis
<220> FEATURE:
<221> NAME/KEY: CDS
<222> LOCATION: (1)..(1863)
<223> OTHER INFORMATION:
<221> NAME/KEY: mat_peptide
<222> LOCATION: (4)..()
<223> OTHER INFORMATION:

<400> SEQUENCE: 1

```
atg agc tgg ctc acg gaa gaa gac atc cgg cgc tgg gaa agc ggt acg        48
Met Ser Trp Leu Thr Glu Glu Asp Ile Arg Arg Trp Glu Ser Gly Thr
 -1   1               5                  10                  15 ttc tac gac agt tac cga aag ctg ggc gcc cat ccc gac gac gaa ggc        96
Phe Tyr Asp Ser Tyr Arg Lys Leu Gly Ala His Pro Asp Asp Glu Gly
                20                  25                  30 acc tgg ttc tgc gtc tgg gcg ccg cat gcc gat ggc gtc tcg gtg ctc       144
Thr Trp Phe Cys Val Trp Ala Pro His Ala Asp Gly Val Ser Val Leu
            35                  40                  45 gga gcg ttc aac gac tgg aat ccg gag gcc aac ccg ctg gag cgc tac       192
Gly Ala Phe Asn Asp Trp Asn Pro Glu Ala Asn Pro Leu Glu Arg Tyr
        50                  55                  60 ggc ggc ggc ctg tgg gcc ggt tac gta ccg gga gcg cgc ccg ggc cac       240
Gly Gly Gly Leu Trp Ala Gly Tyr Val Pro Gly Ala Arg Pro Gly His
 65                  70                  75 acc tac aag tat cgc atc cgg cac ggc ttc tat cag gcc gac aag acg       288
Thr Tyr Lys Tyr Arg Ile Arg His Gly Phe Tyr Gln Ala Asp Lys Thr
 80                  85                  90                  95 gat ccc tac gcc ttc gcc atg gag ccg cct acc ggc agt ccc atc gaa       336
Asp Pro Tyr Ala Phe Ala Met Glu Pro Pro Thr Gly Ser Pro Ile Glu
                100                 105                 110 ggg ctg gcc tcc atc atc acg cgg ctc gac tac acc tgg cac gac gac       384
Gly Leu Ala Ser Ile Ile Thr Arg Leu Asp Tyr Thr Trp His Asp Asp
            115                 120                 125 gaa tgg atg cgg cgc cgg aag ggt ccg gcc agc ctt tac gag ccg gtt       432
Glu Trp Met Arg Arg Arg Lys Gly Pro Ala Ser Leu Tyr Glu Pro Val
        130                 135                 140 tcc atc tac gag gta cat ctg ggc tcc tgg cgt cac aaa cgg ccc ggc       480
Ser Ile Tyr Glu Val His Leu Gly Ser Trp Arg His Lys Arg Pro Gly
    145                 150                 155 gag tcc ttc tct tac cgg gag att gcc gag ccg ctg gcc gac tac gtg       528
Glu Ser Phe Ser Tyr Arg Glu Ile Ala Glu Pro Leu Ala Asp Tyr Val
160                 165                 170                 175 cag gag atg ggc ttc acg cac gtg gag ctg ctg ccc gtc atg gaa cat       576
Gln Glu Met Gly Phe Thr His Val Glu Leu Leu Pro Val Met Glu His
                180                 185                 190
```

```
ccc tac tac ggc tcc tgg ggc tat cag gtg gtg ggc tac tac gcc cca        624
Pro Tyr Tyr Gly Ser Trp Gly Tyr Gln Val Val Gly Tyr Tyr Ala Pro
            195                 200                 205 acg ttt cgc tac gga tca ccc cag gac ctg atg tac ctg atc gac tac        672
Thr Phe Arg Tyr Gly Ser Pro Gln Asp Leu Met Tyr Leu Ile Asp Tyr
            210                 215                 220 ctg cac cag cgc ggc atc ggc gtc atc ctc gac tgg gtc ccg agc cac        720
Leu His Gln Arg Gly Ile Gly Val Ile Leu Asp Trp Val Pro Ser His
            225                 230                 235 ttt gcg gcc gat ccc cag gga ctg gtt ttc ttc gac ggg acc aca ctc        768
Phe Ala Ala Asp Pro Gln Gly Leu Val Phe Phe Asp Gly Thr Thr Leu
240                 245                 250                 255 ttc gaa tac gac gat ccc aag atg cgc tat cac cct gac tgg ggt acg        816
Phe Glu Tyr Asp Asp Pro Lys Met Arg Tyr His Pro Asp Trp Gly Thr
                260                 265                 270 tat gtg ttc gat tac aac aag ccg ggc gta cgc aac ttt ctg att tcc        864
Tyr Val Phe Asp Tyr Asn Lys Pro Gly Val Arg Asn Phe Leu Ile Ser
            275                 280                 285 aac gca ctt ttc tgg ctc gaa aag tac cac gtc gac ggg ctg cgc gtc        912
Asn Ala Leu Phe Trp Leu Glu Lys Tyr His Val Asp Gly Leu Arg Val
            290                 295                 300 gat gcg gtg gct tct atg ctc tac cgg gac tac tca cgc aag gag tgg        960
Asp Ala Val Ala Ser Met Leu Tyr Arg Asp Tyr Ser Arg Lys Glu Trp
305                 310                 315 aca ccc aac atc ttc ggc ggc cgt gaa aac ctg gag gcc att gat ttc       1008
Thr Pro Asn Ile Phe Gly Gly Arg Glu Asn Leu Glu Ala Ile Asp Phe
320                 325                 330                 335 atc aag aaa ttc aac gaa acg gtc tac ctg cac ttc ccc gag gcc atg       1056
Ile Lys Lys Phe Asn Glu Thr Val Tyr Leu His Phe Pro Glu Ala Met
                340                 345                 350 acg atc gcc gag gag tcg acg gcc tgg ccc ggc gtg tcg gcc ccc acc       1104
Thr Ile Ala Glu Glu Ser Thr Ala Trp Pro Gly Val Ser Ala Pro Thr
            355                 360                 365 tac aac aac ggt ctg ggc ttc ctc tac aag tgg aac atg ggc tgg atg       1152
Tyr Asn Asn Gly Leu Gly Phe Leu Tyr Lys Trp Asn Met Gly Trp Met
            370                 375                 380 cac gac acg ctg gac tac atc cag cgc gat ccc atc tac cgc aag tat       1200
His Asp Thr Leu Asp Tyr Ile Gln Arg Asp Pro Ile Tyr Arg Lys Tyr
385                 390                 395 cac cac gac gag ctg acc ttc tcg ctc tgg tac gcc ttt tcg gag cac       1248
His His Asp Glu Leu Thr Phe Ser Leu Trp Tyr Ala Phe Ser Glu His
400                 405                 410                 415 tac gtc ctg ccg ctc tcg cac gac gag gtg gtg cac ggc aag ggc tcg       1296
Tyr Val Leu Pro Leu Ser His Asp Glu Val Val His Gly Lys Gly Ser
            420                 425                 430 ctc tgg ggt aaa atg ccc ggc gac gac tgg cag aag gca gcc aac ttg       1344
Leu Trp Gly Lys Met Pro Gly Asp Asp Trp Gln Lys Ala Ala Asn Leu
            435                 440                 445 cgc ctg ctc ttt ggc cac atg tgg ggc cat ccg ggc aaa aaa ctg ctc       1392
Arg Leu Leu Phe Gly His Met Trp Gly His Pro Gly Lys Lys Leu Leu
            450                 455                 460 ttc atg ggc ggc gag ttc ggc cag cac cac gag tgg aac cac gac acg       1440
Phe Met Gly Gly Glu Phe Gly Gln His His Glu Trp Asn His Asp Thr
465                 470                 475 cag ctc gaa tgg cac ctg ctg gac cag ccc tac cat cga ggt att cag       1488
Gln Leu Glu Trp His Leu Leu Asp Gln Pro Tyr His Arg Gly Ile Gln
480                 485                 490                 495
```

```
ctg tgg gtg tgc gat ctg aac cac ctc tac cgt acg aat ccg gcc ctc      1536
Leu Trp Val Cys Asp Leu Asn His Leu Tyr Arg Thr Asn Pro Ala Leu
        500                 505                 510 tgg cac gac gga ccg gaa ggg ttc gag tgg atc gac ttc agc gac cgc      1584
Trp His Asp Gly Pro Glu Gly Phe Glu Trp Ile Asp Phe Ser Asp Arg
            515                 520                 525 gac cag agc gtg atc tgt tac ctg cgc aag aat gcc ggc cgc atg ctg      1632
Asp Gln Ser Val Ile Cys Tyr Leu Arg Lys Asn Ala Gly Arg Met Leu
        530                 535                 540 ctg ttc gtg ctg aac ttt acg ccc gtg cca cgc gag cac tac cgc gtg      1680
Leu Phe Val Leu Asn Phe Thr Pro Val Pro Arg Glu His Tyr Arg Val
        545                 550                 555 ggc gtg ccg atc ggt ggc ccc tgg cac gag gtg ctc aac agc gac gcg      1728
Gly Val Pro Ile Gly Gly Pro Trp His Glu Val Leu Asn Ser Asp Ala
560                 565                 570                 575 gtg gcc tac ggc ggg agc ggg atg ggc aac ttc ggc cgc gtc gag gcg      1776
Val Ala Tyr Gly Gly Ser Gly Met Gly Asn Phe Gly Arg Val Glu Ala
            580                 585                 590 gtg ccc gag tcc tgg cac ggc cgc ccc ttc cac tta gag ctg acg ctt      1824
Val Pro Glu Ser Trp His Gly Arg Pro Phe His Leu Glu Leu Thr Leu
        595                 600                 605 ccc ccg ctg gcc gcc ctc atc ctg gag ccg gag cac ggg tag              1866
Pro Pro Leu Ala Ala Leu Ile Leu Glu Pro Glu His Gly
        610                 615                 620
```

<210> SEQ ID NO 2
<211> LENGTH: 621
<212> TYPE: PRT
<213> ORGANISM: Rhodothermus obamensis

<400> SEQUENCE: 2

```
Met Ser Trp Leu Thr Glu Glu Asp Ile Arg Arg Trp Glu Ser Gly Thr
 -1   1               5                  10                  15

Phe Tyr Asp Ser Tyr Arg Lys Leu Gly Ala His Pro Asp Asp Glu Gly
                20                  25                  30

Thr Trp Phe Cys Val Trp Ala Pro His Ala Asp Gly Val Ser Val Leu
            35                  40                  45

Gly Ala Phe Asn Asp Trp Asn Pro Glu Ala Asn Pro Leu Glu Arg Tyr
        50                  55                  60

Gly Gly Gly Leu Trp Ala Gly Tyr Val Pro Gly Ala Arg Pro Gly His
 65                  70                  75

Thr Tyr Lys Tyr Arg Ile Arg His Gly Phe Tyr Gln Ala Asp Lys Thr
 80                  85                  90                  95

Asp Pro Tyr Ala Phe Ala Met Glu Pro Pro Thr Gly Ser Pro Ile Glu
                100                 105                 110

Gly Leu Ala Ser Ile Ile Thr Arg Leu Asp Tyr Thr Trp His Asp Asp
            115                 120                 125

Glu Trp Met Arg Arg Arg Lys Gly Pro Ala Ser Leu Tyr Glu Pro Val
        130                 135                 140

Ser Ile Tyr Glu Val His Leu Gly Ser Trp Arg His Lys Arg Pro Gly
145                 150                 155

Glu Ser Phe Ser Tyr Arg Glu Ile Ala Glu Pro Leu Ala Asp Tyr Val
160                 165                 170                 175

Gln Glu Met Gly Phe Thr His Val Glu Leu Leu Pro Val Met Glu His
                180                 185                 190

Pro Tyr Tyr Gly Ser Trp Gly Tyr Gln Val Val Gly Tyr Tyr Ala Pro
            195                 200                 205
```

-continued

```
Thr Phe Arg Tyr Gly Ser Pro Gln Asp Leu Met Tyr Leu Ile Asp Tyr
        210                 215                 220

Leu His Gln Arg Gly Ile Gly Val Ile Leu Asp Trp Val Pro Ser His
        225                 230                 235

Phe Ala Ala Asp Pro Gln Gly Leu Val Phe Phe Asp Gly Thr Thr Leu
240                 245                 250                 255

Phe Glu Tyr Asp Asp Pro Lys Met Arg Tyr His Pro Asp Trp Gly Thr
                260                 265                 270

Tyr Val Phe Asp Tyr Asn Lys Pro Gly Val Arg Asn Phe Leu Ile Ser
                275                 280                 285

Asn Ala Leu Phe Trp Leu Glu Lys Tyr His Val Asp Gly Leu Arg Val
        290                 295                 300

Asp Ala Val Ala Ser Met Leu Tyr Arg Asp Tyr Ser Arg Lys Glu Trp
305                 310                 315

Thr Pro Asn Ile Phe Gly Gly Arg Glu Asn Leu Glu Ala Ile Asp Phe
320                 325                 330                 335

Ile Lys Lys Phe Asn Glu Thr Val Tyr Leu His Phe Pro Glu Ala Met
                340                 345                 350

Thr Ile Ala Glu Glu Ser Thr Ala Trp Pro Gly Val Ser Ala Pro Thr
                355                 360                 365

Tyr Asn Asn Gly Leu Gly Phe Leu Tyr Lys Trp Asn Met Gly Trp Met
        370                 375                 380

His Asp Thr Leu Asp Tyr Ile Gln Arg Asp Pro Ile Tyr Arg Lys Tyr
385                 390                 395

His His Asp Glu Leu Thr Phe Ser Leu Trp Tyr Ala Phe Ser Glu His
400                 405                 410                 415

Tyr Val Leu Pro Leu Ser His Asp Glu Val His Gly Lys Gly Ser
                420                 425                 430

Leu Trp Gly Lys Met Pro Gly Asp Asp Trp Gln Lys Ala Ala Asn Leu
        435                 440                 445

Arg Leu Leu Phe Gly His Met Trp Gly His Pro Gly Lys Lys Leu Leu
        450                 455                 460

Phe Met Gly Gly Glu Phe Gly Gln His His Glu Trp Asn His Asp Thr
465                 470                 475

Gln Leu Glu Trp His Leu Leu Asp Gln Pro Tyr His Arg Gly Ile Gln
480                 485                 490                 495

Leu Trp Val Cys Asp Leu Asn His Leu Tyr Arg Thr Asn Pro Ala Leu
                500                 505                 510

Trp His Asp Gly Pro Glu Gly Phe Glu Trp Ile Asp Phe Ser Asp Arg
        515                 520                 525

Asp Gln Ser Val Ile Cys Tyr Leu Arg Lys Asn Ala Gly Arg Met Leu
        530                 535                 540

Leu Phe Val Leu Asn Phe Thr Pro Val Pro Arg Glu His Tyr Arg Val
545                 550                 555

Gly Val Pro Ile Gly Gly Pro Trp His Glu Val Leu Asn Ser Asp Ala
560                 565                 570                 575

Val Ala Tyr Gly Gly Ser Gly Met Gly Asn Phe Gly Arg Val Glu Ala
                580                 585                 590

Val Pro Glu Ser Trp His Gly Arg Pro Phe His Leu Glu Leu Thr Leu
                595                 600                 605

Pro Pro Leu Ala Ala Leu Ile Leu Glu Pro Glu His Gly
            610                 615                 620
```

POLYPEPTIDES HAVING BRANCHING ENZYME ACTIVITY AND NUCLEIC ACIDS ENCODING SAME

CROSS-REFERENCE TO RELATED APPLICATIONS

This application claims priority under 35 U.S.C. 119 of Danish application PA 1999 00431 filed on Mar. 29, 1999, and U.S. application No. 60/129,608 filed on Apr. 16, 1999, the contents of which are fully incorporated herein by reference.

BACKGROUND OF THE INVENTION

1. Field of the Invention

The present invention relates to isolated polypeptides having branching enzyme activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Branching enzyme (EC 2.4.1.18) hereinafter denoted BE, catalyzes transglycosylation to form the alpha-1,6-glucosidic linkages (branch points) of glycogen and amylopectin in microorganisms, plants and higher organisms. Glycogen and amylopectin are highly branched starch materials used for energy storage in microorganisms, plants and higher organisms. Not only does BE form a branch between different molecules (intermolecular transfer), it also catalyzes the transfer of a multi-branched glucan to another site on the same molecule (intramolecular transfer).

Highly branched starch materials have unique properties like high solubility, low viscosity and less tendency to retrograde compared to unmodified starch, which make them interesting for use in adhesive compositions including surface sizing and coating in the paper industry as described in EP 0 690 170, food and drink additives and anti-starch retrogradation agents as described in U.S. Pat. No. 4,454,161.

Branching enzymes from several different organisms have been isolated and disclosed, e.g.: U.S. Pat. No. 4,454,161 describes a BE from *Bacillus megaterium;* Boyer and Preiss, Biochemistry, vol. 16 (16), pp. 3693–3699, 1977, describe a BE from *Escherichia coli;* Zevenhuizen, Biochem. Biophys. Acta (81), pp. 608–611, 1964, describes a BE from *Arthrobacter globiformis;* Walker and Builder, Eur. J. of Biochem., vol. 20 (1), pp. 14–21, 1971, describe a BE from *Streptococcus mitis;* Kiel et al., Gene, vol. 78 (1), pp. 9–18, 1989, describe a BE from the cyanobacterium Synechococcus sp. PCC7942; Rumbak et al., Journal of Bacteriology, vol. 173 (21), pp. 6732–6741, 1991, describe a BE from Butyrivibrio fibrisolvens; Kiel et al., DNA Sequence, vol. 3 (4), pp. 221–232, 1992, describe a BE from *Bacillus caldolyticus.*

A common characteristic of the above mentioned references is that none of the reported temperature optima are higher than 45° C. Only two branching enzymes have been disclosed which are characterized by having a higher temperature optimum: Kiel et al., Molecular & General Genetics, vol. 230 (1–2), pp. 136–144, 1991 (also in EP 0 418 945): a *Bacillus stearothermophilus* 1503-4R branching enzyme having a temperature optimum of 53° C.; and Takata et al., Applied and Environmental Microbiology, vol. 60 (9), pp. 3096–3104, 1994: a *Bacillus stearothermophilus* TRBE14 branching enzyme having a temperature optimum of around 50° C.

Because of the increased reaction rates obtained at higher temperatures it is industrially advantageous to use branching enzymes with a high temperature optimum. Thereby a higher capacity is obtainable with the same amount of enzyme, and a better production economy is achieved. Furthermore it is beneficial to run processes at high temperatures due to prevention of infections.

It is an object of the present invention to provide improved polypeptides having branching enzyme activity and nucleic acids encoding the polypeptides.

SUMMARY OF THE INVENTION

The present invention relates to isolated polypeptides having branching enzyme activity, and a temperature optimum of at least 60° C.

The present invention also relates to isolated nucleic acid sequences encoding the polypeptides and to nucleic acid constructs, vectors, and host cells comprising the nucleic acid sequences as well as methods for producing and using the polypeptides.

DETAILED DESCRIPTION OF THE INVENTION

Polypeptides Having Branching Enzyme Activity

"branching enzyme activity" is 1,4-alpha-glucan branching activity which catalyzes the formation of 1,6-alpha-glucosidic linkages of glycogen or amylopectin (EC 2.4.1.18). For purposes of the present invention, branching enzyme activity may be determined according to the modified version of the procedure described by Takata et al., Applied and Environmental Microbiology (1994), p. 3097 (assay A), which is described in the Materials and Methods section herein under the heading "Branching enzyme activity".

In a first aspect, the present invention relates to isolated polypeptides having branching enzyme activity, and having a temperature optimum of at least 60° C.; preferably the temperature optimum is in the range of 60° C. to 120° C.; more preferably the temperature optimum is in the range of 60° C. to 100° C.; even more preferably the temperature optimum is in the range of 60° C. to 80° C.; most preferably the temperature optimum is in the range of 60° C. to 70° C.; and even most preferably the temperature optimum is 65° C.

In a first embodiment, the polypeptides of the present invention retain about 70% relative activity in the range of pH 6 to pH 8; preferably about 80% relative activity in the range of pH 6 to pH 7; more preferably the pH optimum is around pH 7.

The conditions used for determining the temperature and pH optima are those described in the Materials and Methods section herein under the heading "Branching enzyme activity".

In a second embodiment, the polypeptides of the present invention have an amino acid sequence which has a degree of homology to amino acids 2 to 621 of SEQ ID NO:2 (i.e. the mature polypeptide) or to the amino acid sequence encoded by the nucleic acid sequence contained in plasmid pT7Blue contained in *E. coli* DSM 12607 of at least about 65%, preferably at least about 70%, more preferably at least about 80%, even more preferably at least about 90%, most preferably at least about 95%, and even most preferably at least about 97%, which have branching enzyme activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2.

For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA", Methods in Enzymology, 183:63–98). Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680). Multiple alignment of DNA sequences may be done using the protein alignment as a template, replacing the amino acids with the corresponding codon from the DNA sequence.

Preferably, the polypeptides of the present invention comprise the amino acid sequence of SEQ ID NO:2 or an allelic variant thereof; or a fragment thereof that has branching enzyme activity. In a more preferred embodiment, the polypeptide of the present invention comprises the amino acid sequence of SEQ ID NO:2. In another preferred embodiment, the polypeptide of the present invention consists of the amino acid sequence of SEQ ID NO:2 or an allelic variant thereof; or a fragment thereof that has branching enzyme activity. In another preferred embodiment, the polypeptide of the present invention consists of the amino acid sequence of SEQ ID NO:2.

A fragment of SEQ ID NO:2 is a polypeptide having one or more amino acids deleted from the amino and/or carboxyl terminus of this amino acid sequence.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a third embodiment, the polypeptides of the present invention have branching enzyme activity which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) the nucleotides of SEQ ID NO:1, (ii) the cDNA sequence contained in the nucleotides of SEQ ID NO:1, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). The subsequence of SEQ ID NO:1 may be at least 100 nucleotides or preferably at least 200 nucleotides. Moreover, the subsequence may encode a polypeptide fragment which has branching enzyme activity. The polypeptides may also be allelic variants or fragments of the polypeptides that have branching enzyme activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having branching enzyme activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having branching enzyme activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is the nucleic acid sequence contained in plasmid pT7Blue, which is contained in *Escherichia coli* DSM 12607 (see Example 1), wherein the nucleic acid sequence encodes a polypeptide having branching enzyme activity.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing posthybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SSC plus 0.1% SDS for 15 minutes and twice each for 15 minutes using 6×SSC at 5° C. to 10° C. below the calculated $T_m$.

In a fourth embodiment, the present invention relates to variants having BE activity of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a fifth embodiment, the polypeptides of the present invention have immunochemical identity or partial immunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the branching enzyme activity of the polypeptide of SEQ ID NO:2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium*

*bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptide is a *Rhodothermus obamensis,* or *Rhodothermus marinus* polypeptide.

In a more preferred embodiment, the polypeptide is a *Rhodothermus obamensis* polypeptide, and most preferably the polypeptide of coding region of the sequence contained in plasmid pT7Blue that is contained in *Escherichia coli* DSM 12607 (see Example 1), e.g., the polypeptide with the amino acid sequence of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of *Rhodothermus obamensis* are defined by Sako et al., International Journal of Systematic Bacteriology, Vol. 46 (4) pp. 1099–1104 (1996).

Strains of these species are readily accessible to the public in a number of culture collections, such as the American Type Culture Collection (ATCC), Deutsche Sammlung von Mikroorganismen und Zellkulturen GmbH (DSMZ), Japan Collection of Microorganisms (JCM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-branching enzyme polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pT7Blue that is contained in *Escherichia coli* DSM 12607 (see Example 1). The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 that have branching enzyme activity.

A subsequence of SEQ ID NO:1 is a nucleic acid sequence encompassed by SEQ ID NO:1 except that one or more nucleotides from the 5' and/or 3' end have been deleted.

The present invention also relates to mutant nucleic acid sequences comprising at least one mutation in the polypeptide coding sequence of SEQ ID NO:1, in which the mutant nucleic acid sequence encodes a polypeptide which consists of the amino acid sequence of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) as shown in Example 1, or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Rhodothermus, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO:1 (i.e. nucleotides 4 to 1863) of at least about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA" Methods in Enzymology 183:63–98).

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for branching enzyme activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) the nucleotides of SEQ ID NO:1, (ii) the cDNA sequence contained in the nucleotides of SEQ ID NO:1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has branching enzyme activity.

Methods for Producing Mutant Nucleic Acid Sequences

The present invention further relates to methods for producing a mutant nucleic acid sequence, comprising introducing at least one mutation into the polypeptide coding sequence of SEQ ID NO:1 or a subsequence thereof, wherein the mutant nucleic acid sequence encodes a polypeptide which consists of the amino acid sequence of SEQ ID NO:2 or a fragment thereof which has branching enzyme activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearotherimophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis,* or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), SC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus,* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide; and (b) recovering the polypeptide. Preferably, the strain is of the genus Rhodothermus, and more preferably *Rhodothermus obamensis*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the polypeptide coding region of SEQ ID NO:1, wherein the mutant nucleic acid sequence encodes a polypeptide which consists of the amino acids of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having branching enzyme activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and Theological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part.

Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus,* or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens-mediated* gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having branching enzyme activity of the present invention under conditions conducive for production of the polypeptide; and (b) recovering the polypeptide.

Compositions

In a still further aspect, the present invention relates to compositions comprising a polypeptide of the present invention. Preferably, the compositions are enriched in a polypeptide of the present invention. In the present context, the term "enriched" indicates that the branching enzyme activity of the composition has been increased, e.g., with an enrichment factor of 1.1.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Detergent Compositions

The branching enzymes of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the branching enzymes of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins; especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from *H. lanuginosa* (*T. lanuginosus*) as described in EP 258 068 and EP 305 216 or from *H. insolens* as described in WO 96/13580, a Pseudomonas lipase, e.g. from *P. alcaligenes* or *P. pseudoalcaligenes* (EP 218 272), *P. cepacia* (EP 331 376), P. stutzeri (GB 1,372,034), *P. fluorescens*, Pseudomonas sp. strain SD 705 (WO 95/06720 and WO 96/27002), *P. wisconsinensis* (WO 96/12012), a Bacillus lipase, e.g. from *B. subtilis* (Dartois et al. (1993), Biochemica et Biophysica Acta, 1131, 253–360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™ and Lipomax™ (Novo Nordisk A/S).

Amylases: Suitable amylases ($\alpha$ and/or $\beta$) include those of bacterial or fungal origin. Chemically modified or protein engineered mutants are included. Amylases include, for example, $\alpha$-amylases obtained from Bacillus, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are polyethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the branching enzymes of the invention, may be added in an amount corresponding to 0.01–100 mg of enzyme protein per liter of wash liqour, preferably 0.05–5 mg of enzyme protein per liter of wash liqour, in particular 0.1–1 mg of enzyme protein per liter of wash liqour.

The branching enzymes of the invention may additionally be incorporated in the detergent formulations disclosed in WO 97/07202, which is hereby incorporated as reference.

Uses

The present invention is also directed to methods for using the polypeptides having branching enzyme activity. For instance, the polypeptides of the invention may be used for modification of starch or starch containing materials so as to improve the properties of such materials.

Examples of materials that can be modified with BE include native starch (unmodified) of all types (potato, maize, wheat), waxy starches, high amylose starches, amylose, amylopectin, chemically modified starches including dextrins, converted starch, crosslinked starch (di-starch phosphate), starch ethers and starch esters (starch acetate, hydroxyalkylated starch, octenyl-succinate starch).

The BE of the invention is useful for modification of a starch-like material, as described above, to make the modified material better suited for its intended purpose, e.g. in the preparation of food products as described in U.S. Pat. No. 4,454,161, e.g. food and drink compositions, food additive compositions, pharmaceutical preparations, sizing agents, adhesives etc. Normally starch materials modified with BE has a high solubility, low viscosity and less tendency to retrograde compared to unmodified starch. These properties can be used to improve the properties of food products prepared from the starch-like material, especially the storage stability of such products. Examples of food products are: bread, desserts, cakes, snacks, noodles and pasta, baby food, sport drinks, processed foods that are frozen or stored cold and pet foods. Enzymatical modification can be performed either on a starch-like material separately before addition to the food product or by adding the enzyme to the food material before or just after cooking, making the modification directly in the food.

For surface sizing and coating of paper high solubility, low viscosity and good stability of the used starch solutions are very important making BE modified starch relevant for these applications as shown in EP 0 690 170.

The present invention is further described by the following examples, which should not be construed as limiting the scope of the invention.

EXAMPLE 1

Materials and Methods

*Rhodothermus obamensis* (JCM 9785) was obtained from Japan Collection of Microorganisms, The Institute of Physical and Chemical Research, Wako, Saitama 351–0198, Japan.

Molecular cloning techniques are described in J. Sambrook, E. F. Fritsch, and T. Maniatis, 1989, *Molecular Cloning, A Laboratory Manual,* 2nd edition, Cold Spring Harbor, N.Y.

The following commercial plasmids/vectors were used:
pT7Blue (Invitrogen, Netherlands)
pBluescript SK(–) (Stratagene, U.S.A.)
pBAD/Myc-HisA (Invitrogen, Netherlands).

The following strains were used for transformation and protein expression:
TOP10 *E. coli (Invitrogen, Netherlands)*
*E. coli DH*12S (GIBCO BRL, Life Technologies, U.S.A.)

SB growth medium (DIFCO #0123-17-3) is composed of:
trypton/pepton, 32 g/l;
yeast extract, 20 g/l;
NaCl, 5 g/l;
5N NaOH, 1 ml/l.

Chemicals used as buffers and substrates were commercial products of at least reagent grade.

Branching Enzyme Activity

BE activity was determined according to a modified version of the procedure described by Takata et al., Applied and Environmental Microbiology (1994), p. 3097 (assay A): 50 μl enzyme solution is mixed with 50 μl substrate solution and incubated for 30 min at testing temperature. The substrate solution is 0.1% type III amylose dissolved in 0.1 M Tris buffer. The reaction is terminated by the addition of 2 ml of iodine reagent. Iodine reagent is made daily from 0.5 ml of stock solution (0.26 g of $I_2$ and 2.6 g of KI in 10 ml of water) mixed with 0.5 ml of 1 N HCl and diluted to 130 ml. The mixture is incubated for 15 minutes at room temperature to stabilize the color. Activity is measured as difference in $A_{660}$ between a tested sample and a control in which cell extract is replaced by water. One unit of branching enzyme activity is defined as the amount of enzyme that can decrease the $A_{660}$ of the amylose-iodine complex by 1% per minute at 60° C., pH 7.0.

Preparation of a R. obamensis gIgB Probe

Primers a) (SEQ ID NO:3) and b) (SEQ ID NO:4) were designed (based on alignment of reported bacterial glgB sequences), prepared and used in a polymerase chain reaction (PCR) with genomic DNA from *Rhodothermus obamensis*.

SEQ ID NO:3, PCR primer a) (forward):
5'-GAGCACCCCYTCGACGGCAGTTGG-3'
SEQ ID NO:4, PCR primer b) (reverse):
5'-CATCCAICCWAKRTTCCA-3'
I=inosine
K=G or T
R=A or G
W=A or T
Y=C or T Reaction components were mixed [genomic DNA, 0.1 ng/μl; dNTPs 0.125 mM each; $Mg^{2+}$, 2.5 mM; primer, 2 pM each; Taq polymerase 0.025 U/μl in 1× buffer (Roche Diagnostics, Japan)] and submitted for PCR under the following conditions:

TABLE 1

| Step | Temperature | Time |
| --- | --- | --- |
| 1 | 94° C. | 5 minutes |
| 2 | 50° C. | 45 seconds |
| 3 | 72° C. | 1 minute |
| 4 | 94° C. | 45 seconds |
| 5 | 50° C. | 45 seconds |
| 6 | 72° C. | 1 minute |
| 7 | 4° C. | forever |

Step 4 to step 6 were repeated 30 times.

The PCR reaction mixture was separated on an agarose gel, and the expected size of the amplified glgB PCR fragments was calculated from *E. coli* glgB sequence data, resulting in approx. 580 bp. These fragments were gel-purified with QIAquick (QIAGEN, Japan), and then ligated into a pT7Blue vector using Takara ligation kit ver. 2 (Takara, Japan). The ligation mixture was purified with phenol/chloroform, and then transformed into *E. coli* DH12S by electroporation. The plasmid (pMSra8) from the obtained transformant was checked by restriction enzyme digestion to confirm the size of the *Rhodothermus obamensis* glgB insert.

Cloning of R. obamensis glgB Gene

Using the inserted fragment of pMSra8 as a R. obamensis glgB probe, Southern hybridization was performed on digested genomic DNA from R. obamensis to select convenient restriction enzymes for generating subclones. A hybridized BamHI fragment of 3.5-kb was selected for a glgB subclone. Therefore, R. obamensis genomic DNA was digested with BamHI, and the size-fractionated DNA was cut out from agarose gels and cloned into pBluescript SK(−). The BamHI sub-library was made by transforming the ligated clones into *E. coli* DH12S cells. Colony lift was performed on transformants of the BamHI sub-library using Hybond-N+membranes (Amersham Pharmacia Biotech, Japan), and then hybridized to the DIG-labeled *R. obamensis* glgB probe. Positive colonies were picked and inserts were checked by PCR. Plasmids from selected colonies were prepared and sequenced revealing that the 3.5 kb BamHI fragment were missing the 5'-terminal of glgB (pMSra10). Accordingly another sub-library made from *R. obamensis* genomic DNA double-digested with KpnI and SalI was screened with the *R. obamensis* glgb probe to recover the 5'-terminal of *R. obamensis* glgB (pMSra29). The whole sequence of structural glgB was obtained from pMSra10 and pMSra29, and PCR primers (SEQ ID NO:5 and SEQ ID NO:6) for amplification of the whole glgB gene was designed from this sequence.

Construction of Expression Vectors

By using primers c) (SEQ ID NO:5) and d) (SEQ ID NO:6) which include respectively a BspHI and a HindIII restriction enzyme site, the whole glgB gene was PCR-amplified from *Rhodothermus obamensis* genomic DNA (to avoid mutations during the PCR reaction Expand High Fidelity from Boehringer Mannheim was used). Cutting the PCR-amplified fragment with BspHI and HindIII allowed directionally cloning into a pBAD/Myc-HisA vector digested with NcoI and HindIII. The resulting vector pMSra33 produced *R. obamensis* BE after transformation in TOP10 *E. coli* and induction with arabinose.

SEQ ID NO:5, Primer c); PCR primer (forward) for amplification of the *Rhodothermus obamensis* glgb gene. Underlined nucleotides introduce the BsPHI site:
5'-TTCCTCATGAGCTGGCTCACGGAAGAAGACA-3'

SEQ ID NO:6, Primer d); PCR primer (reverse) for amplification of the *Rhodothermus obamensis* glgB gene. Underlined nucleotides introduce the HindIII site:
5'-GTTTAAAGCTTTTCAGGACGGCTACC-3'

Biological Deposit DSM 12607

Plasmid pT7Blue with the complete *Rhodothermus obamensis* glgB gene (SEQ ID NO:1) was also transformed in *E. coli* DH12S, which was deposited at DSMZ as DSM 12607 (described in Deposit of Biological Material).

Protein Expression

R. obamensis BE was heterologously expressed in TOP10 *E. coli* strain transformed with pMSra33. The *E. coli* cells were incubated in SB medium with 100 μg/ml ampicillin at 28° C. overnight. 0.0002% arabinose was added for induction of expression. Cells were spinned down by centrifugation and resuspended in 20 mM phosphate buffer (pH 6.0). The amount of buffer corresponded to 1/20 of growth media. Cells were then sonicated and debris was removed by centrifugation.

Removing Endogenous Amylolytic Activity from *E. coli*

By removing all endogenous amylolytic activity from the *E. coli* extract, it becomes possible to use the iodine method (Takata et al., Applied and Environmental Microbiology (1994), p. 3097) to detect expressed BE activity. Accordingly it was tested if heat-treatment could be used to eliminate endogenous amylolytic activity from the host *E. coli* strain with the pBAD/Myc-HisA vector and no glgB insert (negative control). The results showed that a 60° C./20 min. treatment was enough to heat-kill background amylolytic activity measured with the amylose-iodine assay described by Takata et al., where there was no activity detected.

Partial Purification of *R.Obamensis* BE Variant Y397C+L419P

Sequencing of an expressed *R. obamensis* BE reveiled that two changes compared to the mature amino acid sequence of SEQ ID NO:2 had been introduced during the PCR process:
a) Tyr397 was changed to Cys397
b) Leu419 was changed to Pro419.
This BE variant is hereinafter denoted "Y397C+L419P".

*R.obamensis* BE with the substitutions Y397C+L419P expressed in *E.coli* was partially purified by ion-exchange and hydroxyapatite column chromatography. Heat treated cell extract was dialyzed and applied to Super-Q Toyopeal (22 mm×200 mm, TOSOH), then eluted with linear gradient of 0 to 0.6 M NaCl in 50 mM potassium phosphate buffer (pH 7.4). The fractions that had branching enzyme activity were collected and applied to Macro-prep Ceramic Hydroxyapatite Type I (14 mm×100 mm, BioRad), then eluted with gradient of 5 to 400 mM sodium phosphate (pH 6.5). Fractions showing activity were collected. It showed one major band with a couple of minor bands on SDS-PAGE with Coomassie brilliant blue strain.

Branching Linkage Formation

The formation of a-1,6-branching linkage was confirmed by the modified version of branching linkage assay (BL assay, Takeda et al., Carbohydrate Research, 240 253–260 (1993)). The used substrate was 0.5% type III amylose (Sigma) dissolved in 100 mM Tris-HCl (pH 7.5). The substrate (90 μl) and enzyme solution (10 μl) was mixed and incubated at 60° C. for 30 minutes, then the reaction was terminated by boiling for 4 minutes. After addition of 10 μl of 1 M acetate buffer pH 4.1, either 5 μl of isoamylase (1 mg/ml, Hayashibara Co.Ltd.) or 5 μl of deionized water was added to the reaction mixture. It was incubated at 45° C. for 45 minutes. The reaction solution was then added 460 μl of ice-cold ethanol and kept on ice for 10 minutes. Precipitated saccharides were harvested by centrifugation at 12,000 rpm for 5 minutes and vacuum dried once, then dissolved again in 8 μl of 1N NaOH and 292 μl of deionized water. Reducing power of the solution was measured by using the modified 3,5-dinitrosalycylic acid (DNS) method (Luchsinger and Cornesky, 1962). DNS solution was prepared by dissolving 0.05 g of 3,5-dinitrosalycylic acid in 10 ml of 2N NaOH at first, then 3 g of Rochelle salt was added to the solution, and finally total volume was adjusted to 15 ml with deionized water. Sample solution (0.2–0.3 ml) was mixed with 0.4 ml of DNS solution and boiled for 5 minutes. After cooling with running water, 1.8 ml of water was added to the reaction mixture and absorbance at 525 nm was measured. The amount of reducing ends was estimated as equivalent to glucose amount. Partially purified sample of Y397C+L419P was used for the measurement of branching linkage formation. As shown in table 5, reducing ends were produced with the isoamylase treatment, that indicated α-1,6-branching linkage was formed by Y397C+L419P.

TABLE 2

| Experiment number | Isoamylase treatment | Reducing ends (μmol) |
|---|---|---|
| Exp. 1 | + | 0.43 |
|  | none | 0 |
| Exp. 2 | + | 0.17 |
|  | none | 0.04 |

EXAMPLE 2

Effect of Temperature and pH for BE Variant Y397C+L419P

The temperature and pH optima were evaluated for BE variant Y397C+L419P (described in Example 1).

The assay used for BE activity measurement was performed as described in Materials and Methods. To avoid endogenous amylolytic activity from *E. coli* expressing the *R. obamensis* BE, the cell extracts were pre-heated to 60° C. for at least 20 minutes and debris was removed by centrifugation. The pre-heated cell extract was then submitted for assays and analyzed for BE activity.

In the pH optimum assay, different buffers were used to prepare substrate solutions:

| pH < 4 | 0.1 M sodium citrate |
| 4 < pH < 6 | 0.1 M sodium acetate |
| 6 < pH < 10 | 0.1 M Tris |
| pH > 10 | 0.1 M glysylglycine. |

The enzyme (Y397C+L419P) was incubated at the indicated temperature for 30 minutes at pH 7.0. Branching enzyme activity was measured as described above. The experiments were performed at least in triplicate; mean values and std. deviations are shown in table 2 and table 3 below.

The data show the optimum temperature of Y397C+L419P to be around 65° C.

TABLE 3

| Temperature (° C.) | Relative activity (%) Y397C + L419P |
|---|---|
| 30 | 39 +/− 4 |
| 40 | 61 +/− 3 |
| 50 | 64 +/− 8 |
| 55 | 93 +/− 4 |
| 60 | 93 +/− 4 |
| 65 | 97 +/− 3 |
| 68 | 94 +/− 4 |
| 70 | 78 +/− 3 |
| 72 | 57 +/− 2 |
| 75 | 54 +/− 7 |
| 80 | 12 +/− 6 |
| 90 | 9 +/− 3 |

TABLE 4

| Temperature (° C.) | Remaining activity (%) Y397C + L419P |
|---|---|
| 60 | 99 +/− 1 |
| 65 | 100 +/− 0 |
| 70 | 103 +/− 3 |
| 75 | 82 +/− 1 |
| 80 | 2 +/− 3 |
| 85 | 2 +/− 3 |
| 90 | ND |

The pH activity experiments were done at 60° C., and the enzyme was incubated for 30 minutes. The experiments were performed at least in triplicate; mean values and std. deviations are shown in table 4 below. The data indicate that Y397C+L419P has a broad pH optimum of about pH 5 to about pH 8.

TABLE 5

| pH | Relative activity (%)<br>Y397C + L419P |
|---|---|
| 5.3 | 43 +/- 3 |
| 6.3 | 91 +/- 1 |
| 6.7 | 98 +/- 3 |
| 7.6 | 73 +/- 3 |
| 9.0 | 21 +/- 1 |
| 9.3 | 15 +/- 2 |

EXAMPLE 3
Cyclo Dextrin Preparation by BE Variant Y397C+L419P

Rice amylopectin (Motyl B, Shimada Chemical, Japan) was treated with R.obamensis BE with the substitutions Y397C+L419P (described in Example 1) (400 units/g starch) in Tris-HCl buffer (pH 7) at 50° C. for 18 hours. After removing debris by centrifugation at 15,000 rpm for 10 minutes, 2 volumes of ethanol was added to the solution and precipitated dextrin was recovered and dried. About 67 g of dextrin was obtained from 100 g of rice amylopectin. If intramolecular branching linkage has occurred by enzyme treatment, cyclic dextrin that is tolerant to glucoamylase should be obtained. One gram of above mentioned dextrin was treated with 1500 units of glucoamylase (Rhizopus sp. Wako Pure Chemicals, Japan) at pH 4.1, 40° C. for 18 hours, and the resulting dextrin was recovered by ethanol. About 200 mg of dextrin was obtained. There was no dextrin obtained with the treatment in presence of acid α-amylase. Glucoamylase resistant dextrin was treated again with only glucoamylase (0.9 units/g dextrin) or in the combination of glucoamylase and isoamylase (0.9 units and 29 units per g dextrin, respectively) at pH 4.5, 40° C. for 16 hours. As the result, 90% of dextrin was recovered with glucoamylase solely, while only 10% dextrin remained after the treatment in the presence of isoamylase. It indicated that the cyclic dextrin was formed by intramolecular α-1,6-branching linkage catalyzed by Y397C+L419P.

EXAMPLE 4
Expression of R.obamensis BE in Aspergillus
Host Organism

Aspergillus oryzae BECh2 is described in Danish patent application PA 1999 01726. It is a mutant of JaL228 (described in W098/123000), which is a mutant of IFO4177.
Transformation of A.oxyzae Aspergillus oryzae strain BECh2 was inoculated in 100 ml of YPG medium and incubated at 32° C. for 16 hours with stirring at 80 rpm. Grown mycelia was collected by filtration followed by washing with 0.6 M KCl and re-suspended in 30 ml of 0.6 M KCl containing Glucanex® (available from Novo Nordisk) at the concentration of 30 µl/ml. The mixture was incubated at 32° C. with the agitation at 60 rpm until protoplasts were formed. After filtration to remove the remained mycelia, protoplasts were collected by centrifugation and washed with STC buffer twice. The protoplasts were counted with a hematitometer and re-suspended in a solution of STC:STPC:DMSO (8:2:0.1) to a final concentration of $1.2 \times 10^7$ protoplasts/ml. About 4 µg of DNA was added to 100 µl of protoplast solution, mixed gently and incubated on ice for 30 minutes. 1 µl STPC buffer was added to the mixture and incubated at 37° C. for another 30 minutes. After the addition of 10 ml of Cove top agarose pre-warmed at 50° C., the reaction mixture was poured onto COVE agar plates. The plates were incubated at 32° C. for 5 days or until transformants appeared.
Media and Buffer Solution COVE: per liter 342.3 g sucrose, 20 ml COVE salt solution, 10 mM acetamide, 15 mM CsCl$_2$, 30 g Agar noble (Difco)

COVE salt solution: per liter 26 g KCl, 26 g MgSO$_4$-7H$_2$O, 76 g KH$_2$PO$_4$, 50ml Cove trace metals.

Cove trace metals: per liter 0.04 g NaB$_4$O$_7$-10H$_2$O, 0.4 g CuSO$_4$-5H$_2$O, 1.2 g FeSO$_4$-7H$_2$O, 0.7 g MnSO$_4$-H$_2$O, 0.7 g Na$_2$MoO$_2$-2H$_2$O, 0.7 g ZnSO$_4$-7H$_2$O.

AMG trace metals: per liter 14.3 g ZnSO$_4$-7H$_2$O, 2.5 g CuSO$_4$-5H$_2$O, 0.5 g NiCl$_2$, 13.8 g FeSO$_4$, 8.5 g MnSO$_4$, 3.0 g citric acid.

YPG: per liter 4 g yeast extract, 1 g KH$_2$PO$_4$, 0.5 g MgSO$_4$-7H$_2$O, 5 g glucose, pH 6.0.

STC: 0.8 M Sorbitol, 25 mM Tris pH 8, 25 mM CaCl$_2$.

STPC: 40% PEG4000 in STC buffer.

Cove top agarose: per liter 342.3 g sucrose, 20 ml COVE salt solution, 10 mM Acetamide, 10 g low melt agarose.

MS-9: per liter 30 g soybean powder, 20 g glycerol, pH 6.0.

MDU-2Bp: per liter 45 g maltose-1H$_2$O, 7 g yeast extract, 12 g KH$_2$PO$_4$, 1 g MgSO$_4$-7H$_2$O, 2 g K$_2$SO$_4$, 5 g Urea, 1 g NaCl, 0.5 ml AMG trace metal solution pH 5.0.

SDS-PAGE and Western Blotting

SDS polyacrylamide electrophoresis was carried out using the commercialized gel PAGEL AE6000 NPU-7.5L (7.5T%) with the apparatus AE-6400 (Atto, Japan) following the provided protocol. Separated protein in a gel was transferred to a Clear Blot membrane-P AE-6665 (Atto, Japan) using AE-6677 Horizon blot (Atto, Japan). Detection of the protein was employed with Immuno Blot Assay Kit (BioRad).

Construction of Expression Plasmids of R.obamensis glgB for Aspergillus

R. obamensis glgB gene was amplified from R.obamensis genomic DNA using the primers sets of a) & b), or a) & c) to introduce the restriction enzyme site BglII and XhoI at each end. Primer c) gives the sequence of c-myc epitope comprising Glu-Gln-Lys-Leu-Ile-Ser-Glu-Glu-Asp-Leu at the C-terminal glgB.

a) 5'-GAAGATCTAT GAGCTGGCTC ACGGAAGAAG ACATCCGGCG CTGGGAAA-3'
b) 5'-CCGCTCGAGC TACCCGTGCT CCGGCTCCAG GATGAGGGCG GCCA-3'
c) 5'-CCGCTCGAGC TACAGGTCCT CTTCGGAGAT GAGCTTCTGC TCCCCGTGCT CCGGCTCCAG GATGAGGGCG GCCA-3'

Reaction components, i.e. 40 ng of chromosome DNA of R.obamensis, 300 pmol of each primer, 0.2 mM of dNTPs and 2.6 units of DNA polymerase of Expand™ High Fidelity PCR system (Boehringer), were mixed in the provided buffer and submitted for PCR under the following conditions.

TABLE 6

| Step | Temperature | Time |
|---|---|---|
| 1 | 94° C. | 2 mins |
| 2 | 94° C. | 15 sec |
| 3 | 55° C. | 30 sec |
| 4 | 72° C. | 90 sec |
| 5 | 94° C. | 15 sec |
| 6 | 55° C. | 30 sec |
| 7 | 72° C. | 90 + 20 sec/cycle |
| 8 | 72° C. | 7 mins |

Step 2 to step 4 were repeated 10 times, and step 5 to step 7 were repeated 20 cycles.

The amplified 1.9 Kb fragment was purified with QIA gel extraction kit (Qiagen) and after digestion with BglII and XhoI, it was ligated into pCaHj483 digested with BamHI and XhoI. The plasmid pCaHj483 has *Aspergillus niger* neutral amylase promoter, *Aspergillus nidulans* TPI leader sequence, *Aspergillus niger* glucoamylase terminator and *Aspergillus nidulans* amdS gene as a marker. The plasmid obtained with the primer set a) & b) was termed pIH28 and the one obtained with the primer set of a) & c) was designated pIH29.

Expression of *R.obamensis* glgB in *A. oxyzae*

The expression plasmids, pIH28 and pIH29, were digested with NotI and resulting 6 kb fragments containing the expression cassette of *R.obamensis* glgB were purified with QIA gel extraction kit. *A.oryzae* BECh2 was transformed with each fragment and selection positive transformants were isolated. Transformant was inoculated to 100 ml of MS-9 in 500 ml of shaking flask and cultivated at 32° C. for 1 day and 3 ml of each culture was transferred to 100 ml of MDU-2Bp in shaking flask to cultivate at 32° C. for 2–3 days. Grown cells were harvested by centrifugation at 3500 rpm for 15 minutes. About 0.1 g of collected cells was suspended in 100 μl of 2× conc. of sample loading buffer (100 mM Tris-HCl (pH 6.8), 200 mM Dithiothreitol, 4% SDS, 0.2% Bromophenol blue and 20% glycerol) and boiled for 5 minutes. After centrifugation at 14000 rpm for 5 minutes, 10 μl of supernatant was applied to a polyacrylamide gel, and subjected for electrophoresis in the running buffer (25 mM Tris, 0.1% SDS, 192 mM Glycine) at 20 mA per gel. Resulting gel was stained with Coomassie brilliant blue. Positive transformants showed the protein band of expected size of *R.obamensis* glgB, 72 kDa. The gel applied with the extract of transformant with c-myc tag was subjected for western blotting using Anti-myc antibody (Invitrogen) as primary antibody and Anti-mouse IgG (Sigma) as secondary antibody. Positive signals were obtained at the position corresponding to 72 kDa.

EXAMPLE 5

*R.obamensis* BE assay and effect of temperature and pH

To inactivate endogenous amylase activity from host strain, the cell extract was heated at 65° C. for 30 minutes. Activity was measured as described before.

The pH activity profile was measured at 65° C. and the temperature activity profile was obtained at pH 7. The experiments were performed either in duplicate or in triplet and the means and standard deviations are shown below.

Temperature stability was measured on the *R.obamensis* BE without c-myc tag as follows; enzyme solution containing 30–50 units/ml (pH 7) was incubated at the different temperatures for 30 minutes, and then remaining branching enzyme activity was measured.

The data indicate the optimum pH and optimum temperature of *R.obamensis* BE to be around pH 7 and 65° C., respectively. The presence of c-myc tag did not affect the pH and temperature profile.

TABLE 7

| pH | Relative activity (%) BE1-5 (w/o myc-tag) | Relative activity (%) BBe28 (with tag) |
| --- | --- | --- |
| 2.4 | 8 +/−1 | 6 +/− 2 |
| 3.0 | 7 +/− 2 | 7 +/− 2 |
| 4.0 | 10 +/− 1 | 8 +/− 1 |

TABLE 7-continued

| pH | Relative activity (%) BE1-5 (w/o myc-tag) | Relative activity (%) BBe28 (with tag) |
| --- | --- | --- |
| 5.2 | 74 +/− 8 | 67 +/− 1 |
| 6.3 | 87 +/− 2 | 77 +/− 5 |
| 7.1 | 97 +/− 1 | 97 +/− 3 |
| 7.8 | 93 +/− 1 | 89 +/− 4 |
| 8.6 | 88 +/− 1 | 81 +/− 1 |
| 9.5 | 83 +/− 4 | 75 +/− 1 |
| 10.6 | 12 +/− 2 | 16 +/− 1 |

TABLE 8

| Temperature (° C.) | Relative activity (%) BE1-5 (w/o myc-tag) | Relative activity (%) BBe28 (with tag) |
| --- | --- | --- |
| 30 | 4 +/− 1 | 1 +/− 4 |
| 40 | 11 +/− 1 | 6 +/− 1 |
| 50 | 35 +/− 1 | 24 +/− 0 |
| 55 | 60 +/− 5 | 50 +/− 0 |
| 60 | 80 +/− 1 | 71 +/− 1 |
| 63 | 92 +/− 3 | 88 +/− 2 |
| 65 | 96 +/− 4 | 94 +/− 4 |
| 68 | 93 +/− 3 | 90 +/− 4 |
| 70 | 87 +/− 2 | 86 +/− 1 |
| 73 | 75 +/− 1 | 73 +/− 2 |
| 75 | 59 +/− 5 | 59 +/− 2 |
| 80 | 17 +/− 1 | 12 +/− 2 |

TABLE 9

| Temperature (° C.) | Remaining activity (%) R. obamensis BE |
| --- | --- |
| 60 | 95 +/− 5 |
| 65 | 95 +/− 5 |
| 70 | 88 +/− 3 |
| 75 | 91 +/− 3 |
| 80 | 91 +/− 2 |
| 85 | 83 +/− 1 |
| 90 | 13 +/− 3 |

DEPOSIT OF BIOLOGICAL MATERIAL

An *E. coli* clone containing the BE gene from *Rhodothermus obamensis* inserted into plasmid pT7Blue (see Example 1) has been deposited under the terms of the Budapest Treaty with the Deutsche Sammlung von Mikroorganismen und Zellkulturen GmbH (DSMZ), Mascheroder Weg 1b, D-38124 Braunschweig, Germany, and given the following accession number:

| Deposit | Accession Number | Date of Deposit |
| --- | --- | --- |
| NN049443 | DSM 12607 | 1998 Dec. 23 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated polypeptide having branching enzyme activity selected from the group consisting of:
   a) a polypeptide having an amino acid sequence which has at least 80% homology with amino acids 1 to 620 of the amino acid sequence of SEQ ID NO:2;
   b) a polypeptide having an amino acid sequence which has at least 80% homology with the branching enzyme amino acid sequence encoded by the nucleic acid sequence contained in plasmid pT7Blue contained in *E. coli* DH12S, DSM 12607; and
   c) a polypeptide which is encoded by a nucleic acid sequence which hybridizes under hybridization conditions comprising prehybridization and hybridization at 42° C. in 5×SSPE, 0.3% SDS, 200 µg/ml sheared and denatured salmon sperm DNA, and 35% formamide, followed by washing three times for 15 minutes using 2×SSC, 0.2% SDS at 60° C. with (i) nucleotides 4 to 1863 of the nucleic acid sequence of SEQ ID NO:1, (ii) nucleotides 1 to 1863 of SEQ ID NO:1, or (iii) a full complementary strand of (i), or (ii).

2. The polypeptide of claim 1, having an amino acid sequence which has at least 80% homology with the amino acid sequence of SEQ ID NO:2.

3. The polypeptide of claim 2, having an amino acid sequence which has at least 95% homology with the amino acid sequence of SEQ ID NO:2.

4. The polypeptide of claim 1, comprising or consisting of the amino acid sequence of SEQ ID NO:2, or consisting of a fragment of the amino acid sequence of SEQ ID NO:2.

5. The polypeptide of claim 1, which consists of the amino acid sequence of SEQ ID NO:2 or a variant thereof having the substitutions Y397C+L419P.

6. The polypeptide of claim 1, which is encoded by the nucleic acid sequence contained in plasmid pT7Blue contained in *E. coli* DH12S, DSM 12607.

7. A detergent composition comprising a polypeptide according to claim 1 and a surfactant.

8. An isolated polypeptide having branching enzyme activity comprising a polypeptide having an amino acid sequence which has at least 80% homology with amino acids 1 to 620 of the amino acid sequence of SEQ ID NO:2.

9. The polypeptide of claim 8, having an amino acid sequence which has at least 90% homology with amino acids 1 to 620 of the amino acid sequence of SEQ ID NO:2.

10. The polypeptide of claim 8, having an amino acid sequence which has at least 95% homology with amino acids 1 to 620 of the amino acid sequence of SEQ ID NO:2.

11. The polypeptide of claim 8, having an amino acid sequence which has at least 97% homology with amino acids 1 to 620 of the amino acid sequence of SEQ ID NO:2.

12. An isolated polypeptide having branching enzyme activity comprising a polypeptide having an amino acid sequence which has at least 80% homology with the branching enzyme amino acid sequence encoded by the nucleic acid sequence contained in plasmid pT7Blue contained in *E. coli* DH12S, DSM 12607.

13. The polypeptide of claim 12, having an amino acid sequence which has at least 90% homology with the the branching enzyme amino acid sequence encoded by the nucleic acid sequence contained in plasmid pT7Blue contained in *E. coli* DH12S, DSM 12607.

14. The polypeptide of claim 12, having an amino acid sequence which has at least 95% homology with the the branching enzyme amino acid sequence encoded by the nucleic acid sequence contained in plasmid pT7Blue contained in *E. coli* DH12S, DSM 12607.

15. The polypeptide of claim 12, having an amino acid sequence which has at least 97% homology with the the branching enzyme amino acid sequence encoded by the nucleic acid sequence contained in plasmid pT7Blue contained in *E. coli* DH12S, DSM 12607.

16. An isolated polypeptide having branching enzyme activity comprising a polypeptide which is encoded by a nucleic acid sequence which hybridizes under hybridization conditions comprising prehybridization and hybridization at 42° C. in 5×SSPE, 0.3% SDS, 200 µ/ml sheared and denatured salmon sperm DNA, and 35% formamide, followed by washing three times for 15 minutes using 2×SSC, 0.2% SDS at 60° C. with nucleotides 4 to 1863 of the nucleic acid sequence of SEQ ID NO:1.

17. The polypeptide of claim 16, wherein the hybridization conditions comprise prehybridization and hybridization at 42° C. in 5×SSPE, 0.3% SDS, 200 µg/ml sheared and denatured salmon sperm DNA, and 50% formamide, followed by washing three times for 15 minutes using 2×SSC, 0.2% SDS at 65° C.

18. The polypeptide of claim 16, wherein the hybridization conditions comprise prehybridization and hybridization at 42° C. in 5×SSPE, 0.3% SDS, 200 µg/ml sheared and denatured salmon sperm DNA, and 50% formamide, followed by washing three times for 15 minutes using 2×SSC, 0.2% SDS at 70° C.

\* \* \* \* \*